(12) United States Patent
Shipley et al.

(10) Patent No.: US 8,708,555 B2
(45) Date of Patent: *Apr. 29, 2014

(54) METHODS AND SYSTEMS FOR VERIFYING SENSOR BOND INTEGRITY AND STRUCTURES EMPLOYING SUCH SYSTEMS

(75) Inventors: John L. Shipley, Tremonton, UT (US); Jerry W. Jenson, Thatcher, UT (US); Mark R. Eggett, Brigham City, UT (US); Sorin V. Teles, North Ogden, UT (US); Don W. Wallentine, Mantua, UT (US)

(73) Assignee: Alliant Techsystems Inc., Arlington, VA (US)

(*) Notice: Subject to any disclaimer, the term of this patent is extended or adjusted under 35 U.S.C. 154(b) by 1078 days.

This patent is subject to a terminal disclaimer.

(21) Appl. No.: 12/631,600

(22) Filed: Dec. 4, 2009

(65) Prior Publication Data

US 2010/0131211 A1   May 27, 2010

Related U.S. Application Data

(63) Continuation-in-part of application No. 12/046,553, filed on Mar. 12, 2008, now Pat. No. 8,147,135.

(51) Int. Cl.
*G01N 25/72* (2006.01)
*G01K 11/00* (2006.01)

(52) U.S. Cl.
USPC ............... 374/5; 374/57; 374/121; 374/117

(58) Field of Classification Search
USPC ................. 374/5, 57, 121, 117
See application file for complete search history.

(56) References Cited

U.S. PATENT DOCUMENTS

| | | | |
|---|---|---|---|
| 4,442,718 A | 4/1984 | Komarova et al. |
| 4,831,258 A | 5/1989 | Paulk et al. |
| 5,651,284 A | 7/1997 | Leon |
| 5,709,469 A | 1/1998 | White et al. |
| 5,841,034 A | 11/1998 | Ball |
| 6,026,881 A | 2/2000 | Durso |
| 6,301,971 B1 | 10/2001 | Sykes |
| 6,490,047 B2 | 12/2002 | Siu |
| 6,565,686 B2 | 5/2003 | Bett et al. |

(Continued)

FOREIGN PATENT DOCUMENTS

| JP | 01244351 A | * | 9/1989 |
|---|---|---|---|
| JP | 09101255 A | * | 4/1997 |

*Primary Examiner* — Mirellys Jagan
(74) *Attorney, Agent, or Firm* — TraskBritt

(57) ABSTRACT

Methods and systems are disclosed for determining an amount of bond between a structure and sensor. A method may include performing a process associated with a sensor bonded to a structure and generating measured data in response to the process. The method may further include comparing the measured data to known reference data to determine integrity of a bond between the sensor and the structure. A system may include a sensor system including at least one sensor bonded to a structure. The system may further include a sensing system configured to initiate an application of one or more stimuli to the at least one sensor and monitor a property associated with the at least one sensor. The sensing system may further be configured to determine an amount of bond between the at least one sensor and the structure based on the monitored property. Structures having one or more sensors bonded thereto and an associated sensing system for determining bond integrity between the one or more sensors and the structure are also disclosed.

17 Claims, 14 Drawing Sheets

(56) References Cited

U.S. PATENT DOCUMENTS

| | | |
|---|---|---|
| 6,951,137 B2 | 10/2005 | Smith et al. |
| 7,041,960 B2 | 5/2006 | Sato |
| 7,077,011 B2 | 7/2006 | Johnson et al. |
| 7,425,093 B2 | 9/2008 | Wickersham, Jr. et al. |
| 7,461,560 B2 | 12/2008 | Arms et al. |
| 8,147,135 B2 | 4/2012 | Shipley et al. |
| 2004/0076216 A1* | 4/2004 | Chamberlain et al. .......... 374/57 |
| 2004/0206893 A1* | 10/2004 | Sato ...................... 250/227.14 |
| 2004/0218660 A1 | 11/2004 | Heerdt et al. |
| 2005/0120803 A1* | 6/2005 | Sokol et al. ..................... 73/801 |
| 2005/0147150 A1* | 7/2005 | Wickersham et al. ........ 374/120 |
| 2005/0169346 A1 | 8/2005 | Murray, Jr. et al. |
| 2006/0009865 A1 | 1/2006 | Goldfine et al. |
| 2007/0223557 A1* | 9/2007 | Pevzner et al. ................... 374/5 |
| 2008/0075137 A1* | 3/2008 | Cervantes et al. ................ 374/1 |
| 2009/0168074 A1 | 7/2009 | Monchalin et al. |

* cited by examiner

METHODS AND SYSTEMS FOR VERIFYING SENSOR BOND INTEGRITY AND STRUCTURES EMPLOYING SUCH SYSTEMS

RELATED APPLICATIONS

This application is a continuation-in-part of U.S. patent application Ser. No. 12/046,553 entitled METHOD AND SYSTEMS FOR VERIFYING SENSOR BOND INTEGRITY filed Mar. 12, 2008, now U.S. Pat. No. 8,147,135 issued Apr. 3, 2012 the disclosure of which is hereby incorporated herein in its entirety by reference.

TECHNICAL FIELD

This invention, in various embodiments, relates generally to sensors configured to measure a physical property and, more specifically, methods and systems for verifying the integrity of a bond between a sensor and a structure on, in or with respect to which a physical property is to be measured.

BACKGROUND

A strain gauge is a strain-sensitive device employed to sense strain, such as that caused by stress in the form of tensile or compressive forces applied to a structure. Conventional strain gauges typically employ a strain sensing element adhered to at least one surface on or within the structure such that, when the structure exhibits a strain in response to an applied stress, the resistance of the sensing element changes in proportion to the sensed strain. The measured strain is generally calculated based on the change in resistance in the sensing element as the structure is compressed or elongated, thus exhibiting or manifesting the strain. Strain gauges can be used to measure bending, axial and torsional strain, or a combination of strain effects, on a structure resulting from various applied loads.

Strain gauges may include foil-type strain gauges comprising a pattern of resistive foil mounted on a backing surface. Furthermore, strain gauges may include semiconductor strain gauges, which are often preferred over foil gauges when measuring small amounts of strain. Strain gauges may be attached to a flexible plastic substrate that, in turn, is bonded to the structure for which the strain is to be determined.

A sensing element for a strain gauge is conventionally implemented within a Wheatstone bridge circuit, which converts the sensed resistance to a voltage signal. To obtain the voltage signal, it is generally required to further connect a differential amplifier and a current source to the Wheatstone bridge circuit. FIG. 1 is a schematic diagram of Wheatstone bridge circuit 100 including four branches, one of which may include a resistive transducer, such as a strain gauge 110. The other branches of Wheatstone bridge circuit 100 include resistors $R_1$, $R_2$, and $R_3$. An input DC voltage, or excitation voltage $V_{in}$, is applied between the top and bottom of circuit 100 and an output voltage $V_{out}$ is measured across the middle of circuit 100. When the output voltage is zero, circuit 100 is balanced. As the resistance of one of the branches changes, by a strain of a resistive strain gauge for example, the previously balanced circuit becomes unbalanced. This unbalance causes a voltage $V_{out}$ to appear across the middle of circuit 100. This induced voltage may be measured with a voltmeter or the resistor $R_3$ in the opposite branch may be adjusted to rebalance circuit 100. In either case, the change in resistance that caused the induced voltage may be measured and converted to obtain a degree of strain.

FIG. 2 illustrates a conventional strain sensing system 200. System 200 includes a strain sensor 210 in electrical communication with a sensing system 220. Strain sensor 210 may include circuitry, such as the Wheatstone bridge circuit 100 shown in FIG. 1. Furthermore, strain sensor 210 may be coupled to a structure for sensing strain responsive to stress experienced by the structure due to an applied force or forces. Strain sensor 210 produces an electrical signal that is used by the sensing system 220 for identifying the strain force on the object and presenting the identified force to an observer.

The accuracy of data reported by a sensor, such as a strain gauge, mounted to a structure depends to a high degree on the integrity of the bond, such as an adhesive bond, between the sensor and the structure to which it is secured. It is generally accepted that the adhesive bond (e.g., an epoxy) may break down or debond over time due to various conditions, such as by way of non-limiting example, fatigue, corrosion or bond degradation due to exposure to elements, such as moisture, subjection to temperature extremes, or simply long-term degradation of the adhesive bond over an extended period of time. A sensor which is debonded from a structure even slightly may result in failure or malfunction of the sensor manifested as a complete lack of sensor output and may, at best, provide incorrect strain measurements in the form of a reduced-magnitude or otherwise misleading output. Furthermore, conventional sensors do not always provide sufficient, if any, warning of potential failure or malfunction due to partial or complete disbonding.

The bond between a sensor and a structure of interest to which the sensor is secured is conventionally inspected by visual or tactile means, which are time consuming and often inconclusive. Furthermore, a sensor may reside in a location not accessible to a human inspector, such as within an interior of a structure wall or within a sealed compartment.

There is a need to enhance the efficiency and reliability of measuring a physical property on a structure of interest. Specifically, there is a need for methods, devices, and systems for verifying the integrity of a bond between a sensor for measuring a physical property of a structure and the structure of interest.

BRIEF SUMMARY OF THE INVENTION

An embodiment of the present invention comprises a method of verifying sensor bond integrity. The method may include applying one or more stimuli to a sensor bonded to a structure and monitoring a physical property output associated with the sensor responsive to the one or more stimuli. The method may further include determining an amount of bond between the sensor and the structure based on the monitored physical property output.

Another embodiment of the present invention comprises a method of measuring bond integrity between a sensor and a structure. The method may include performing a process associated with a sensor bonded to a structure and generating measured data in response to the process. Further, the method may include comparing the measured data to known reference data to determine integrity of a bond between the sensor and the structure.

According to another embodiment of the present invention a method of determining integrity of a bond between a sensor and a structure may include measuring an amount of capacitance between a structure and a sensor bonded thereto to generate measured data. Additionally, the method may include comparing the measured data to known reference data to determine integrity of a bond between the sensor and the structure.

Another embodiment of the present invention comprises a method of determining an amount of a bond between a sensor and a structure. The method may comprise stimulating a sensor bonded to a structure and monitoring a property associated with the sensor to generate measured data. Moreover, the method may comprise quantifying a condition of a bond between the sensor and the structure based on the measured data.

According to another embodiment of the present invention a method of determining a condition of a bond between a sensor and a structure may include monitoring an effect of one or more stimuli applied to a sensor bonded to a structure. The method may further include determining a condition of a bond between the sensor and the structure based on the affect of the one or more stimuli.

Another embodiment of the present invention comprises a system. The system may comprise a sensor system including at least one sensor bonded to a structure. The system may further comprise a sensing system coupled to the sensor system and including a signal conditioner. The sensing system may be configured to initiate an application of one or more stimuli to the at least one sensor. The sensing system may be further be configured to monitor a property associated with the at least one sensor and determine a percentage of bond between the at least one sensor and the structure based on the monitored property.

Another embodiment of the present invention includes a system including at least one sensor bonded to a structure. The system may further include a sensing system operably coupled to the at least one sensor and configured to initiate a process to be performed on the at least one sensor. The sensing system may further configured to determine an amount of bond between the at least one sensor and the structure based on a response of the sensor to the process.

Yet another embodiment of the present invention includes a computer-readable media storage medium storing instructions that, when executed by a processor, cause the processor to perform instructions for operating a sensing system according to an embodiment of the present invention.

Yet a further embodiment of the present invention comprises a structure having a sensor system comprising at least one sensor bonded to one or more components thereof, and a sensing system configured to determine at least one of an amount of bond between the at least one sensor and the structure, and a condition of the bond. The structure may have bonded thereto at least one redundant sensor at substantially the same location as the at least one sensor, and the sensing system may be configured to employ the at least one redundant sensor if measured data from the at least one sensor indicates that output from the at least one sensor may be unreliable due to a compromised bond and measured data from the at least one redundant sensor indicates an adequate bond thereof to the structure for sensing.

DETAILED DESCRIPTION OF THE INVENTION

Figure 1:
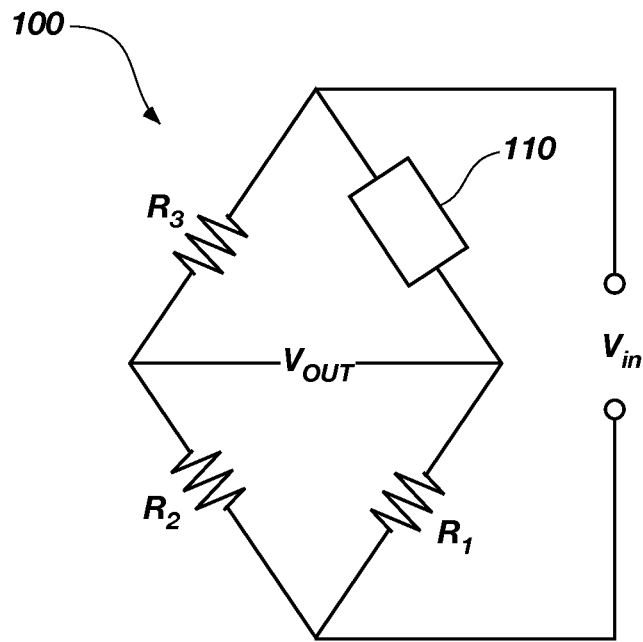
FIG. 1 is a schematic diagram of a Wheatstone bridge circuit incorporating a strain gauge.
Figure 2:
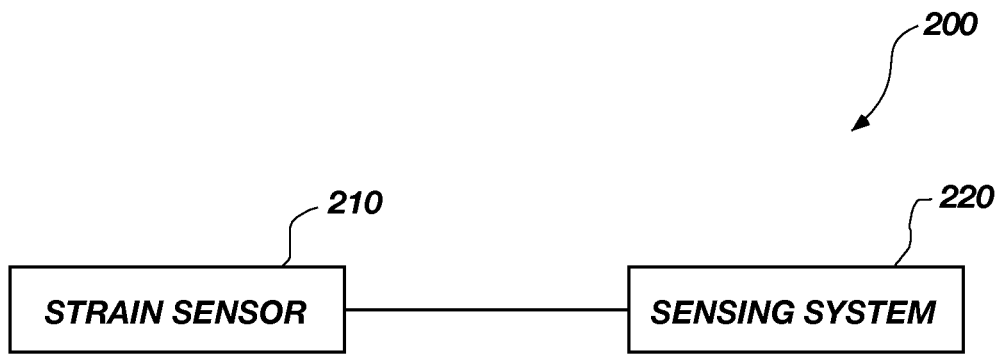
FIG. 2 is a conventional strain sensing system including a strain sensor in electrical communication with a sensing system.

The present invention, in various embodiments, comprises apparatuses and systems for, and methods of, verifying the integrity of a bond between a structure and a sensor attached thereto. In the following description, circuits and functions may be shown in block diagram form in order not to obscure the present invention in unnecessary detail. Conversely, specific circuit implementations shown and described are examples only and should not be construed as the only way to implement the present invention unless specified otherwise herein. Additionally, block definitions and partitioning of logic between various blocks is exemplary of a specific implementation. It will be readily apparent to one of ordinary skill in the art that the present invention may be practiced by numerous other partitioning solutions. For the most part, details concerning timing considerations and the like have been omitted where such details are not necessary to obtain a complete understanding of the present invention and are within the abilities of persons of ordinary skill in the relevant art.

In this description, some drawings may illustrate signals as a single signal for clarity of presentation and description. It will be understood by a person of ordinary skill in the art that the signal may represent a bus of signals, wherein the bus may have a variety of bit widths and the present invention may be implemented on any number of data signals, including a single data signal. In describing embodiments of the present invention, the systems and elements incorporating embodiments of the invention are described to facilitate an enhanced understanding of the function of the described embodiments of the invention as it may be implemented within these systems and elements.

When executed as firmware or software, the instructions for performing the methods and processes described herein may be stored on a computer readable medium. A computer readable medium includes, but is not limited to, magnetic and optical storage devices such as disk drives, magnetic tape, CDs (compact disks), DVDs (digital versatile discs or digital video discs), and semiconductor devices such as RAM, DRAM, ROM, EPROM, and Flash memory.

As described more fully below, various embodiments of the present invention include systems and methods for verifying integrity of a bond between two components, such as, for example, a sensor and a structure. More specifically, various embodiments of the present invention are related to systems and methods for applying a stimulus to a sensor bonded to a structure, monitoring a property associated with the sensor in response to the stimulant, and determining integrity of a bond between the sensor and the structure. Other embodiments may include measuring the property associated with a sensor to generate measured data and comparing the measured data to known reference data to determine integrity of a bond between the sensor and a structure.

As known by one having ordinary skill in the art, a sensor, such as a transducer may be configured to convert a physical property (e.g., temperature (heat), electromagnetic radiation (light, magnetic field, etc.), strain, acceleration, sound intensity) to an electrical property, such as voltage, resistance, or current. Furthermore, as is well known in the art, a sensor may be attached to a structure and may be used to determine a physical property on the structure correlated to output of the sensor. As described above, a strain gauge sensor conventionally employs a strain sensing element adhered to a surface of a structure such that when the structure exhibits a strain, the resistance of the sensing element changes in proportion to the sensed strain. A resistance temperature detector (RTD) sensor also employs a sensing element to provide a change in resistance proportional to a change in temperature of the structure to which the RTD is attached. As such, RTDs and strain gauges produce small changes in resistance in response to a change in a physical property exhibited by the structure such as temperature or strain. For example only, and not by way of limitation, a strain gauge may be attached to a pressure vessel, such as a rocket motor, and used to determine an amount of strain exhibited by the pressure vessel.

Figure 3:
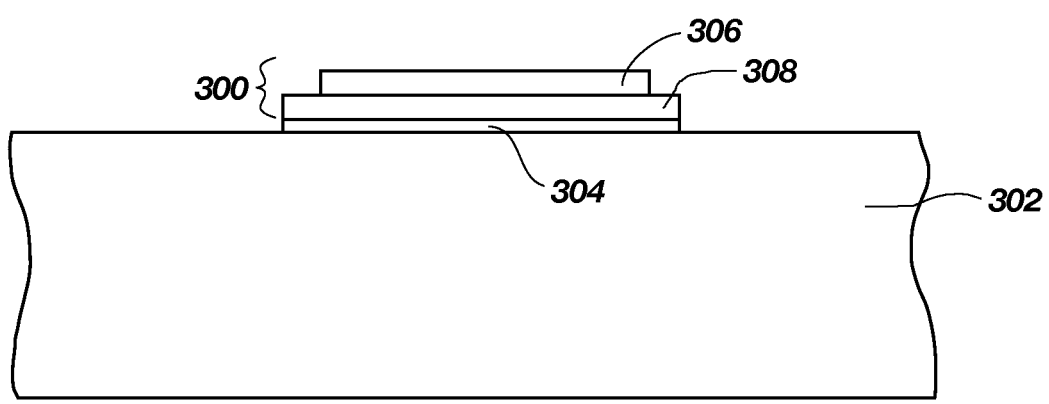
FIG. 3 is a cross-sectional diagram of a sensor bonded to a structure.

Embodiments of the present invention may be applicable to any sensor that may be bonded to one or more components of a structure. FIG. 3 illustrates a sensor 300 attached to a structure 302. For example only, sensor 300 may be configured to measure strain, temperature, pressure, or any combination thereof. For explanation purposes only, sensor 300 may comprise a strain gauge, which may be configured to measure strain due to, for example only, bending, torsion, elongation, or compression experienced by a portion of a structure to which the strain gauge is attached. It is noted that sensor 300 may comprise a foil strain gauge or a bonded semiconductor strain gauge. As a non-limiting example, sensor 300 may include a constantan foil 306 plated on a polyimide layer 308. Sensor 300 may be positioned and affixed to structure 302 by attaching or fastening sensor 300 using an appropriate fastening technique. Such a fastening technique may include bonding sensor 300 to structure 302 using a suitable bonding agent 304, for example, such as an epoxy or other adhesive. As explained above, it is possible for a sensor to debond from a structure for various reasons, including without limitation fatigue or corrosion. The accuracy of the information provided by sensor 300 may depend to a high degree on the integrity of bond between sensor 300 and structure 302. Accordingly, at some level of bonding degradation, the information provided by sensor 300 may not be trustworthy.

An example of a method of determining the integrity of a bond between a sensor and a test structure will first be described in general. Subsequently, a more detailed example with reference to FIGS. 4A and 4B will be provided. Thereafter, output results of tests performed on a sensor will be described in reference to FIGS. 5-8.

Initially, a sensor, adjacent to a structure, may be heated in a quick manner by any means known in the art so as to heat the sensor without heating the structure to any substantial or detectable extent. For example only, heating a sensor may comprise applying a thermal shock for a short duration to the sensor by any method known in the art, such as photo flash heating, electrical heating, or external heating. Photo flash heating may comprise utilizing a flash lamp, as known in the art, and directing it toward the sensor. Furthermore, the sensor may be heated by an external device such as a blower or hair dryer. In addition, as described more fully below, the sensor may be electrically heated by applying an increased or pulsed current or an increased or pulsed voltage to the sensor. Accordingly, after application of a thermal shock, the sensor will register a shift in temperature that will decay over time. Based on the general principles of heat transfer, it will be understood by one having ordinary skill in the art that if the sensor is at least partially debonded from a structure, the temperature of the sensor will increase a greater amount than it would if the sensor was fully bonded to the structure. Also, the thermal expansion of a sensor that is at least partially debonded may be greater than it would be if the sensor was fully bonded. After heating a sensor, the shift in a physical property, such as temperature or strain, and the rate of decay of the shift may be measured over time resulting in measured data. Thereafter, the measured data may be compared to reference data in order to determine an amount of bond (e.g., a percentage of bond) remaining between a sensor and a structure. Stated another way, the bond integrity between a sensor and a structure of interest to which the sensor is affixed may be characterized in terms of percent of an initial, known bond integrity.

Reference data may include voltage, temperature or strain measurements taken from a test sensor with a known amount of bond between the test sensor and a test structure. For example, the measured data may be compared against reference data obtained from tests performed on a model sensor. Furthermore, the reference data may, for example only, include data obtained from earlier tests performed on the same sensor. Furthermore, for example only, the measured data may be compared against reference data obtained by computational methods if the material properties of a test sensor and test structure are known.

Figure 4A:
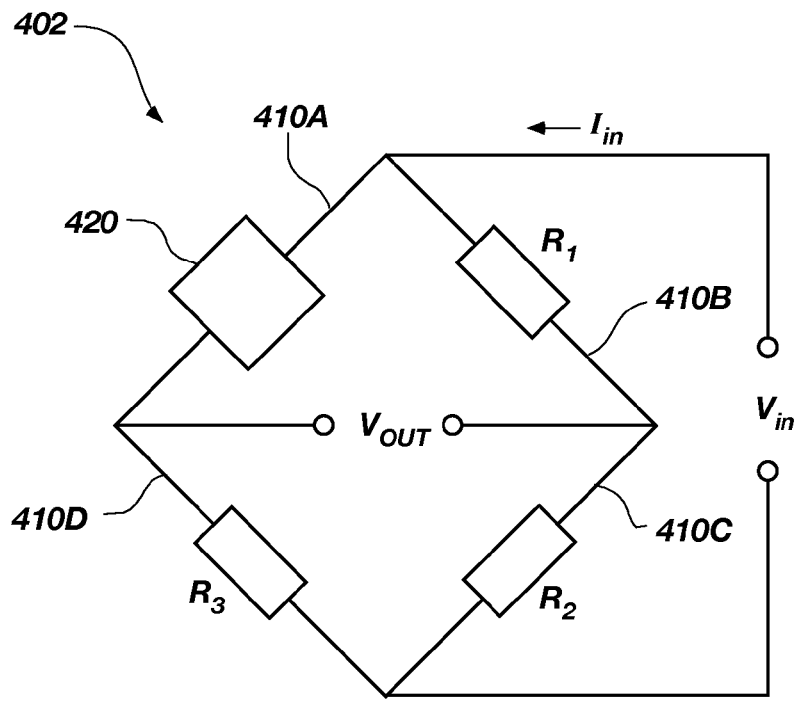
FIG. 4A illustrates a sensor within a measurement circuit suitable for use in accordance with an embodiment of the invention.

A more detailed example of determining the amount or percentage of a bond between a sensor and a structure will now be described. As known by one having ordinary skill in the art, in order to measure a physical property with a bonded sensor, the sensor may be integrated within a measurement circuit configured to measure the changes in an electrical property corresponding to a change in a physical property, such as temperature or strain. For example only, a measurement circuit may include a Wheatstone bridge circuit including at least one sensor configured to measure electrical resistance. FIG. 4A illustrates an example of a Wheatstone bridge circuit 402 having four branches 410A, 410B, 410C, and 410D. Branch 410A may include a sensor 420, and branches 410B, 410C, and 410D may include resistors $R_1$, $R_2$, and $R_3$, respectively. Although Wheatstone bridge circuit 402, as shown in FIG. 4A, includes sensor 420 located within branch 410A, a Wheatstone bridge may take various forms. For example, sensor 420 may be located within branch 410B, 410C, or 410D. Furthermore, although Wheatstone bridge circuit 402 is illustrated as a "quarter" Wheatstone bridge (i.e., only one of the four branches includes a sensor), embodiments of the invention may be applicable to full bridges (i.e., having a sensor within each branch) and half bridges (i.e., two of the four branches include a sensor). For example only, and not by way of limitation, sensor 420 may comprise an RTD, thermistor, or a strain gauge.

Figure 4B:
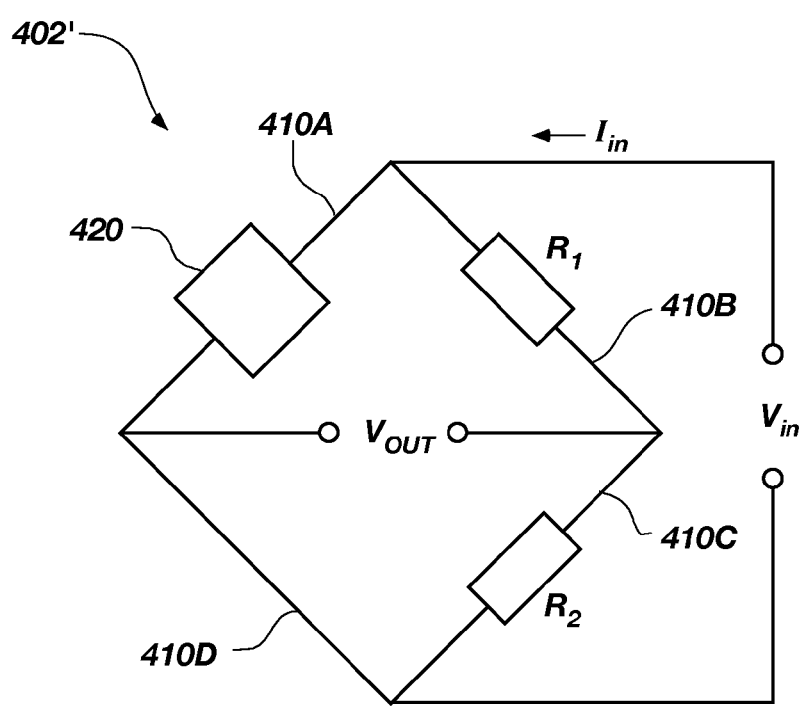
FIG. 4B illustrates the sensor within the measurement circuit of FIG. 4A during application of heat, in accordance with an embodiment of the invention.

Referring to FIGS. 4A and 4B, initially, a thermal shock may be applied to sensor 420 by way of electrical heating. Although the following description discusses applying a thermal shock by way of electrical heating, embodiments of the present invention are not so limited and any method known in the art and suitable for applying a thermal shock to a given sensor in a particular environment is within the scope of the invention. According to one embodiment of the present invention, a thermal shock may be applied to sensor 420 by first supplying a current $I_{in}$ and an input voltage $V_{in}$ to Wheatstone bridge circuit 402. Subsequently, resistor $R_3$, which is in series with sensor 420, may be shorted out, resulting in circuit 402', as shown in FIG. 4B. With resistor $R_3$ shorted out, a voltage across sensor 420 may be approximately doubled due to the entire input voltage $V_{in}$ being applied across sensor 420. As a result, a temperature of sensor 420 may be increased. The application of heat may then be eliminated by removing the short (resulting, again, in circuit 402 illustrated in FIG. 4A) and an output signal, such as voltage $V_{out}$, may be monitored as sensor 420 returns to the pre-thermal shock condition. By methods known in the art, a resistive response and a temperature response of sensor 420 over time may be determined from the response of output voltage $V_{out}$ over time.

Referring again to FIG. 4A, and according to another embodiment of the present invention, a thermal shock may be applied to sensor 420 by supplying an increased voltage (i.e., a voltage greater than $V_{in}$) to Wheatstone bridge circuit 402 for a short period of time (e.g., 0.13 seconds). As a result, the temperature of sensor 420 may be increased. Subsequently, the application of heat may be terminated by decreasing the voltage to $V_{in}$. At any time during the application of heat, or after the application of heat is terminated, a resistive or a temperature response of sensor 420 over time may be monitored as sensor 420 returns to the pre-thermal shock condition.

According to yet another embodiment, a thermal shock may be applied to sensor 420 by supplying an increased current (i.e., a current greater than current $I_{in}$) to Wheatstone bridge circuit 402 for a short period of time and, therefore, increasing the temperature of sensor 420. Subsequently, the application of heat may be terminated by decreasing the current to current $I_{in}$. At any time during the application of heat, or after the application of heat is terminated, a resistive or a temperature response of sensor 420 over time may be monitored as sensor 420 returns to the pre-thermal shock condition.

As mentioned above, embodiments of the invention are not limited to quarter Wheatstone bridge circuits but, rather, embodiments of the present invention may be implemented with full or half Wheatstone bridge circuits. Further, embodiments of the present invention may be implemented without a Wheatstone bridge (e.g., constant current excitation of a single strain gage). As understood by one having ordinary skill in the art, each sensor within a full or half Wheatstone bridge circuit may be individually tested by heating a specific sensor by applying short circuits and/or injecting voltages at appropriate locations within the circuit and monitoring a resistive or temperature response of the sensor during a time period while heating the sensor, during a time period after terminating the application of heat to the senor, or any combinations thereof.

FIGS. 5-8 illustrate results obtained from tests done on a strain gauge according to various bonding percentages between the strain gauge and a structure. In these tests, the strain gauge was heated, for example, for approximately 0.13 second and the output results (i.e., temperature or strain) were monitored with respect to time.

Figure 5:
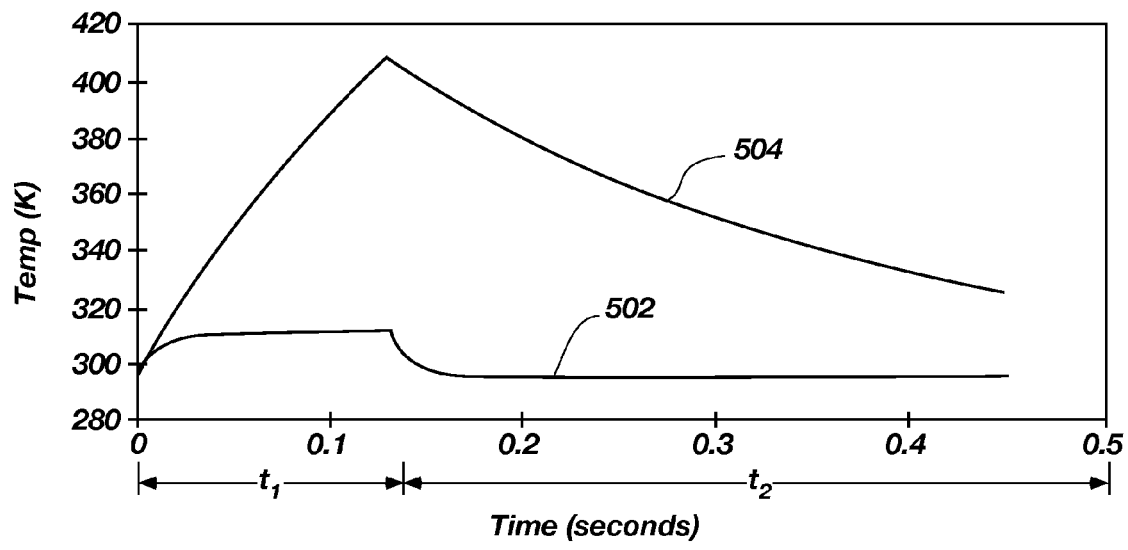
FIG. 5 is a plot illustrating a temperature versus time relationship of a fully bonded sensor and a fully unbonded sensor after application of heat to each sensor.

FIG. 5 is a plot illustrating a comparison of the change of temperature over time for a fully bonded strain gauge and a fully unbonded strain gauge during a first time period $t_1$ wherein heat is applied to the strain gauge, and a second time period $t_2$ immediately following removal of the heat. As shown in FIG. 5, the temperature of a fully unbonded strain gauge (signal 504) quickly increases from approximately 300 Kelvin to above 400 Kelvin during the first time period $t_1$. Subsequently, after ceasing the application of heat, the temperature of the fully unbonded strain gauge decreases toward its original state during time period $t_2$. On the other hand, the temperature of a fully bonded strain gauge (signal 502) increases from approximately 300 Kelvin to approximately 310 Kelvin during the first time period $t_1$. Subsequently, after ceasing the application of heat, the temperature of the fully bonded strain gauge decreases to its original state during time period $t_2$.

Figure 6:
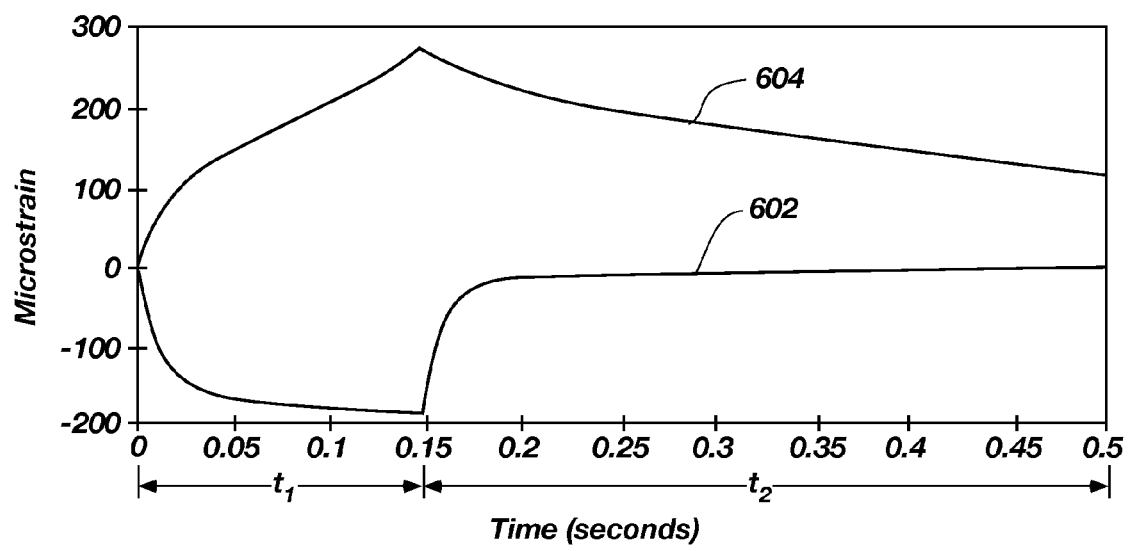
FIG. 6 is a plot illustrating a strain versus time relationship of a fully bonded sensor and a fully unbonded sensor after application of heat to each sensor.

FIG. 6 is a plot illustrating a comparison of the change of strain over time of a fully bonded strain gauge and a fully unbonded strain gauge during a first time period $t_1$ wherein heat is applied to the strain gauge, and a second time period $t_2$ immediately following removal of the heat. As shown in FIG. 6, a fully bonded strain gauge (signal 602) exhibits a decrease in strain during application of heat (i.e., during time period $t_1$). This decrease in strain is due to the fact that a fully bonded strain gauge is constrained from expansion during the application of heat because of the fully bonded configuration. As a result, the fully bonded strain gauge compresses and the strain measured by the strain gauge decreases. After removing the heat, the strain of the fully bonded strain gauge increases to its original state during time period $t_2$. On the other hand, a fully unbonded strain gauge (signal 604) exhibits an increase in strain during application of heat (i.e., during time period $t_1$). This increase in strain is due to fact that a fully unbonded strain gauge is unconstrained and, therefore, expands during the application of heat (i.e., during time period $t_1$). As a result, the strain of the fully unbonded strain gauge increases. After removing the heat, the strain of the fully unbonded strain gauge decreases toward its original state during time period $t_2$.

Figure 7:
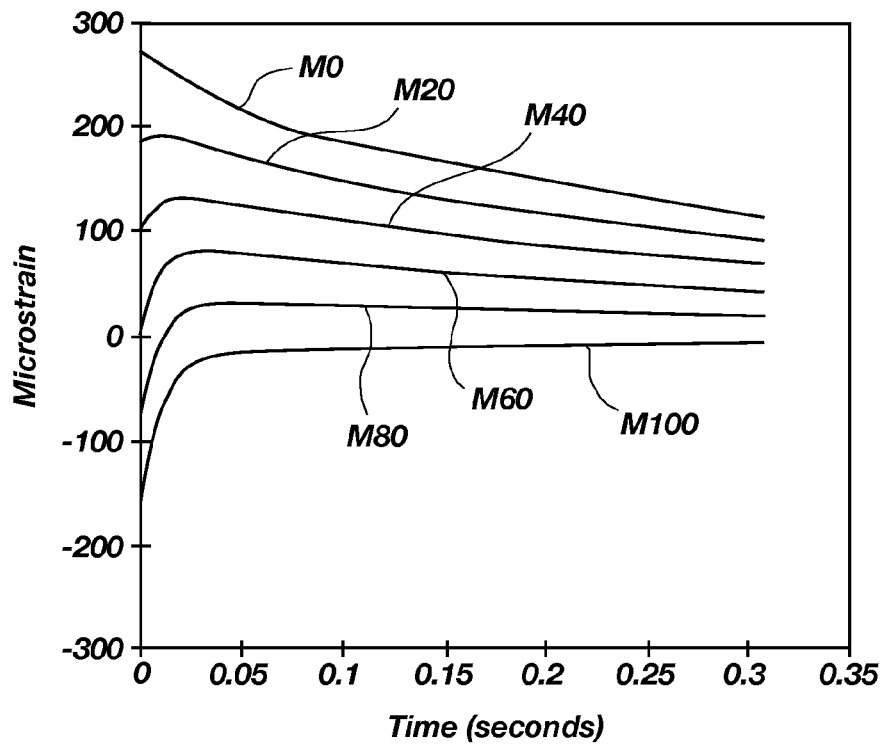
FIG. 7 is a plot of model data illustrating a strain versus time relationship of a model sensor according to various bonding percentages.

FIG. 7 is a plot illustrating reference data including strain signals generated from a model sensor having various bonding percentages between the model sensor and a model test structure. Furthermore, the time period illustrated in FIG. 7 represents a time period immediately following removal of heat to the model sensor. Signals M100, M80, M60, M40, M20, and M0 represent strain signals generated from a model sensor respectively having a 100%, 80%, 60%, 40%, 20%, and 0% bond to a model test structure.

Figure 8:
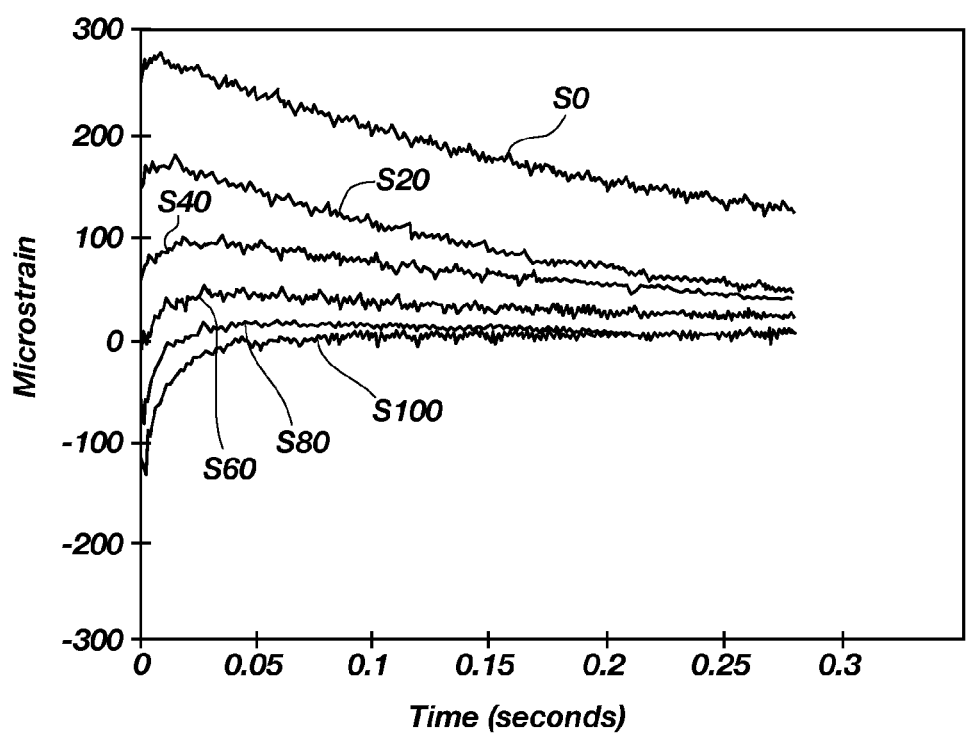
FIG. 8 is a plot of actual measured data illustrating a strain versus time relationship of a sensor according to various bonding percentages.

FIG. 8 is a plot illustrating measured data including strain signals generated from a sensor with various bonding percentages between the sensor and a structure. During an initial test, with the sensor fully bonded (i.e., 100%), the sensor was subjected to a thermal shock during a first time period and an output voltage was monitored over a second time period. Subsequently, a strain measurement was calculated for the second time period resulting in output signal S100. Thereafter, the sensor was partially peeled from the structure creating a bond of approximately 80%, which when subjected to a thermal shock, produced an output signal S80. Similarly, in successive tests, the sensor was peeled away from the test structure to ever-greater degrees, creating bonds of approximately 60%, 40%, 20%, and 0%, which correlate to output signals S60, S40, S20, and S0, respectively.

As mentioned above, reference data, generated from, for example, tests performed on a model sensor or computational methods, may be compared with the measured data (i.e., the shift in temperature or strain and rate of decay of the temperature or strain over time) in order to quantify the percentage of bond existing between the sensor and the structure. For example, the measured data illustrated in FIG. 8 may be compared against the model data illustrated in FIG. 7 in order to approximate an amount of bond between a sensor and a structure.

Although the examples described below include sensors implemented with a Wheatstone bridge circuit, embodiments of the present invention are not so limited, and embodiments of the present invention may include sensors implemented by any acceptable measurement circuit configuration as known by one having ordinary skill in the art. Furthermore, although embodiments of the invention have been described in reference to strain gauge sensors or resistance temperature detector sensors, embodiments of the disclosure may be applicable to any sensor that may be bonded to a structure. Embodiments of the disclosure may also be applicable to internal structures, such as pressure gages and accelerometers.

Figure 9:
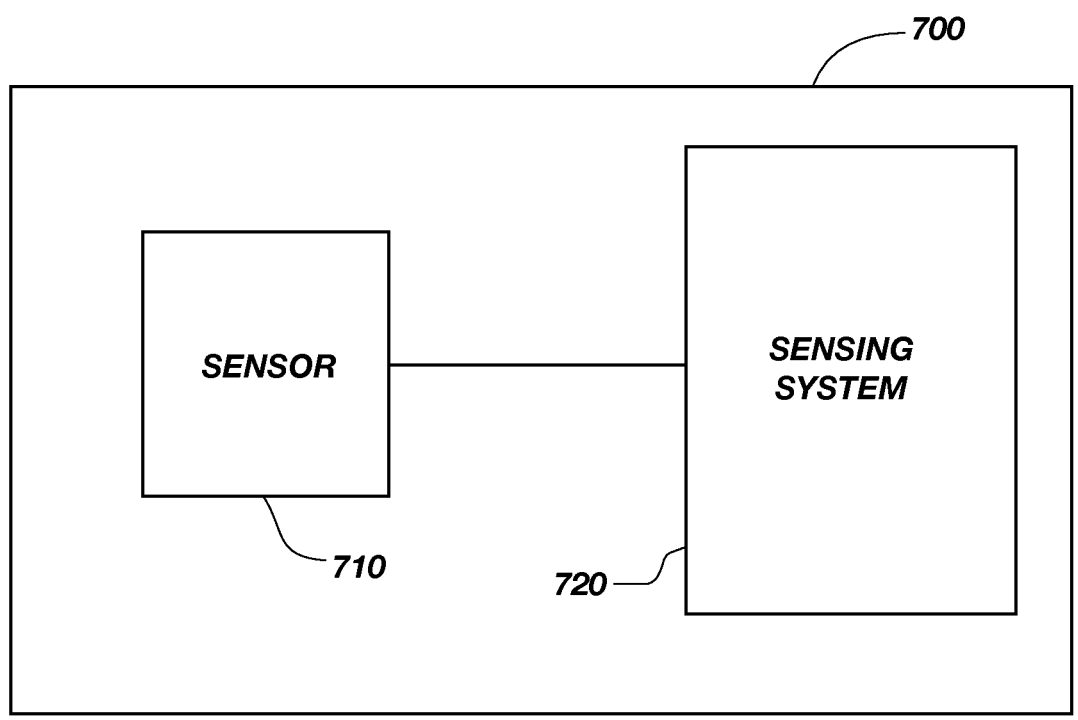
FIG. 9 is a block diagram of a system including a sensor and sensing system, according to an embodiment of the invention.

FIG. 9 illustrates a system 700 including a sensor 710 configured to sense a physical property of a structure attached thereto. Physical properties sensed by sensor 710 may include, for example only, temperature, light, magnetic field, strain, acceleration, or sound intensity. As a non-limiting example, sensor 710 may include a strain gauge or an RTD, as described above. Furthermore, system 700 may be configured as an automated sensing system 720 configured to periodically verify a bond integrity between a structure 302 (see FIG. 3) and sensor 710 attached thereto. Sensing system 720 may be adapted to apply an input voltage and an input current to sensor 710. Furthermore, sensing system 720 may be configured to apply heat to sensor 710 for a short period of time, to remove the heat, and to subsequently receive an output signal from sensor 710. Sensing system 720 may further be configured to monitor the output signal over time, generate measured data (e.g., a physical property, such as temperature or strain) over time, compare the measured data to known reference data, and quantify an amount of bond between sensor 710 and structure 302.

As noted above, reference data may be obtained by computational methods. According to one embodiment, a system (e.g., sensing system 720) may be configured to receive, via a user interface, input data, such as material properties of a sensor of interest (e.g., a thickness of a polyimide layer and a fill factor of a constantan foil), material properties of a structure (i.e., a thickness and a material type) bonded to the sensor of interest, and material properties of a bonding agent (i.e., a material type) between the structure and the sensor of interest. Upon receipt of the input data, the system may be configured to generate model reference data, which may be compared to measured data associated with the sensor of interest to determine an amount of bond between the sensor of interest and the structure.

Figure 10:
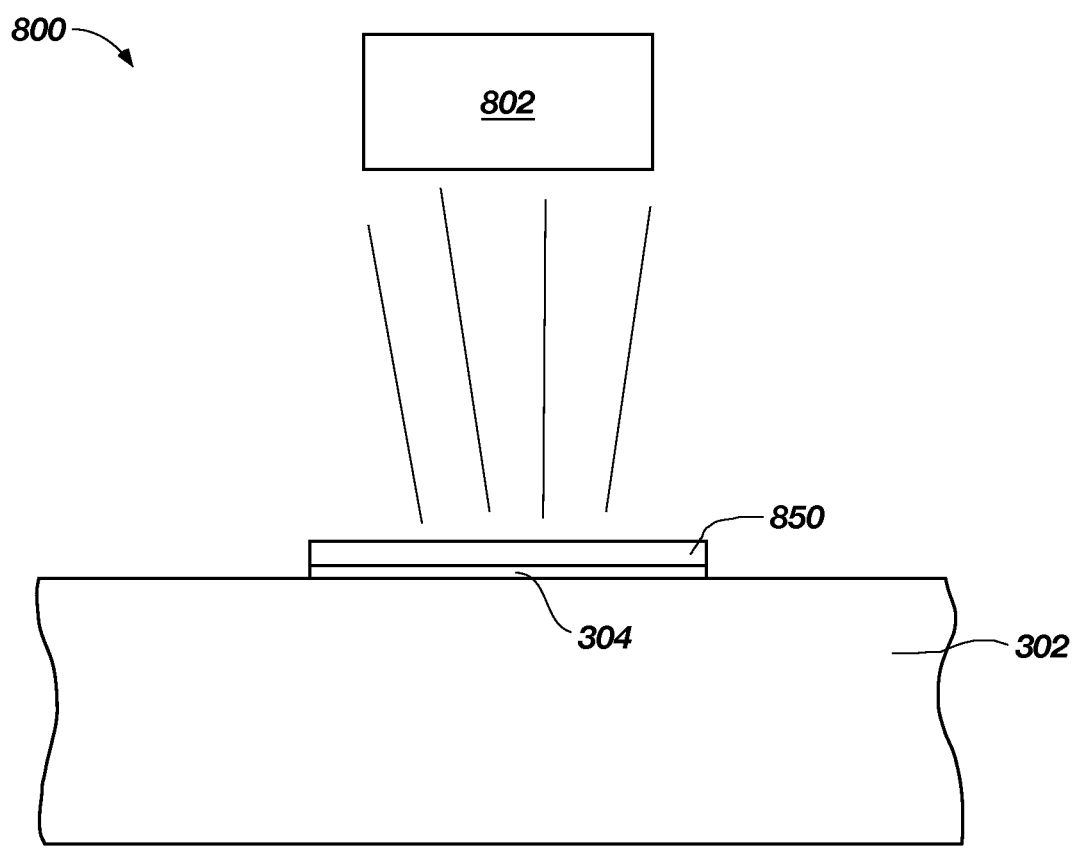
FIG. 10 illustrates a system including an infrared sensor and a sensor bonded to a structure, in accordance with an embodiment of the present invention.

FIG. 10 illustrates a system 800 including an infrared sensor 802 and a sensor 850 bonded to structure 302 via bonding agent 304, in accordance with various embodiments of the present invention. By way of example only, sensor 850 may comprise a sensor configured to measure a physical property, such as strain, temperature, pressure, or any combination thereof. As a more specific example, sensor 850 may comprise a strain gauge (e.g., a bonded semiconductor strain gauge or a foil strain gauge). Further, infrared sensor 802 may comprise, for example only, an infrared camera.

A contemplated method of determining integrity of a bond between sensor 850 and structure 302 will now be described. Initially, a process associated with sensor 850 may be performed. The process may comprise, for example, applying one or more stimuli to sensor 850. Furthermore, during application of the one or more stimuli, after termination of the one or more stimuli, or a combination thereof, one or more properties (e.g., a physical property such as temperature) associated with sensor 850 may be monitored. Stated another way, an effect of the one or more stimuli on sensor 850 may be monitored.

Figure 11:
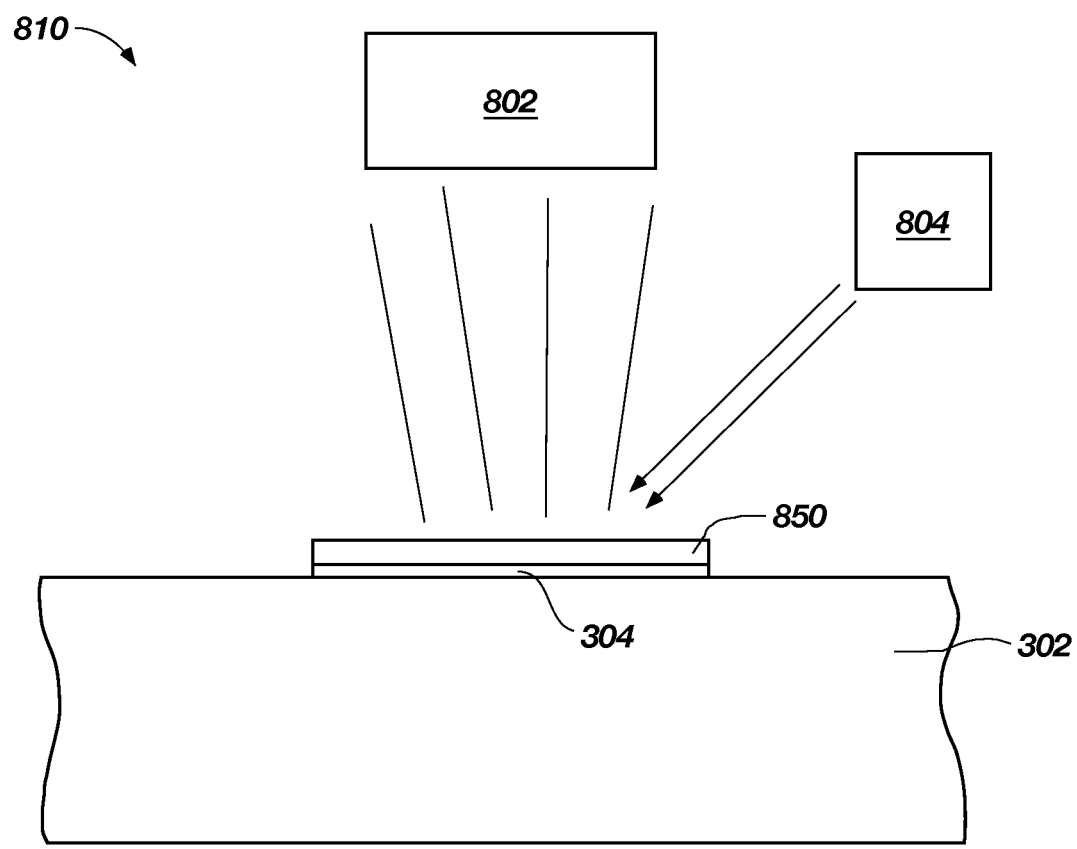
FIG. 11 illustrates another system including an infrared sensor, a sensor bonded to a structure, and an illumination source, in accordance with an embodiment of the present invention.

More specially, for example, the contemplated method may include heating sensor 850 by applying a thermal shock thereto for a short duration by any suitable method described herein, such as photo flash heating, electrical heating, or external heating. According to one embodiment, sensor 850 may be heated by applying an increased current or an increased voltage thereto, as described above with reference to FIGS. 4A and 4B. According to another embodiment, sensor 850 may be heated via an illumination source 804, as illustrated in a system 810 depicted in FIG. 11. Illumination source 804 may also be referred to herein as a light source. With reference to FIG. 11, illumination source 804 may comprise a flash lamp suitable to apply a thermal shock to sensor 850. Hence, in one contemplated operation of system 810, sensor 850 may be heated via photo flash heating. More specifically, sensor 850 may be heated by a burst of light generated by illumination source 804. In accordance with another embodiment, illumination source 804 may comprise a laser or electron beam generator suitable to apply a thermal shock to sensor 850. Accordingly, in another contemplated operation of system 810, sensor 850 may be heated via a laser beam or electron beam transmitted from illumination source 804.

Moreover, with reference to FIGS. 10 and 11, during application of a thermal shock to sensor 850, after termination of the thermal shock, or both, the temperature of sensor 850 may be monitored by infrared sensor 802. More specifically, the temperature along a surface of sensor 850 proximate structure 302 may be monitored by infrared sensor 802. As will be understood by one having ordinary skill in the art, structure 302 may function as a heat sink and, therefore, if sensor 850 is at least partially debonded from structure 302, the temperature at the debonded region of sensor 850 will be greater than it would be if the region was fully bonded to structure 302. Stated another way, because air, vapor, or vacuum may exist between structure 302 and a disbonded region of sensor 850, during application of a thermal shock, a temperature of sensor 850 at the disbonded region may increase more quickly than it would have had the region been bonded. Furthermore, after termination of the thermal shock, a temperature of sensor 850 at a disbonded region may decrease less quickly than it would have had the region been bonded.

Temperature measurements associated with sensor 850 taken during application of a thermal shock, after termination of the thermal shock, or a combination thereof, may be used as measured data. Further, the measured data may be used to determine a condition of a bond between sensor 850 and structure 302. More specifically, in a similar manner as described above with reference to FIGS. 3-8, the measured data may be compared to known reference data in order to determine an amount of bond (e.g., a percentage of bond) between sensor 850 and structure 302. As mentioned above, reference data may include data obtained from a test sensor with a known amount of bond between the test sensor and a test structure, data obtained from earlier tests performed on sensor 850, or data obtained by computational methods if the material properties of sensor 850 and structure 302 are known. Additionally, it is noted that a thermal image generated by infrared sensor 802 may be analyzed to identify one or more regions where sensor 850 has debonded from structure 302.

Figure 12:
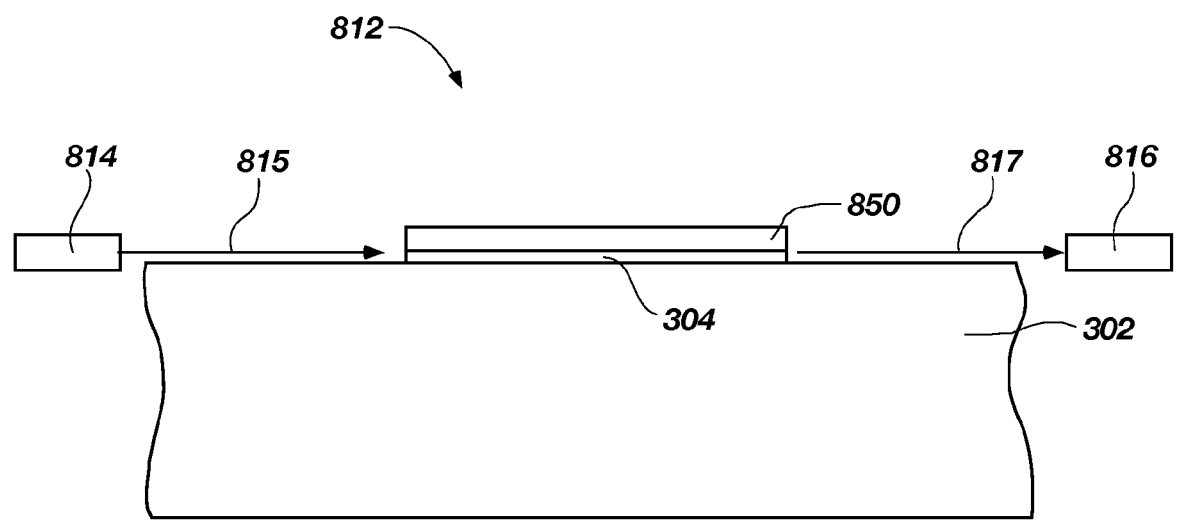
FIG. 12 illustrates another system including a sensor bonded to a structure, and a wave generator and a receiver proximate the sensor, according to an embodiment of the present invention.

FIG. 12 illustrates another system 812 according to an embodiment of the present invention. System 812 includes sensor 850, which is bonded to structure 302 via bonding agent 304. System 812 further includes a wave generator 814 configured and positioned for transmitting energy waves, such as acoustic waves, at known frequencies and known amplitudes toward bonding agent 304 and adjacent surfaces of sensor 850 and structure 302. The waves may be transmitted through structure 302 or through a medium (e.g., air, water, a gel, or a compliant substrate placed on structure 302). It is noted that bonding agent 304 along with surfaces of sensor 850 and structure 302 adjacent bonding agent 304 may be commonly referred to herein as a "sensor bond region." For example only, wave generator 814 may be configured to transmit a broadband pulse (i.e., a plurality of ultrasound waves across a range of known frequencies and at known amplitudes) in a direction (depicted by arrow 815) toward the sensor bond region. As more specific examples, wave generator 814 may comprise an ultrasound (UT) transducer, a pulsed laser, or a surface acoustic wave (SAW) device. In addition, system 812 may include a receiver 816, which is positioned on a side of sensor 850 opposite to wave generator 814 and is configured to receive a broadband pulse having a plurality of waves propagating at measurable frequencies and measurable amplitudes and in a direction depicted by arrow 817. It is noted that wave generator 814 and receiver 816 may be configured as a common device.

A contemplated method of utilizing system 812 to determine integrity of a bond between sensor 850 and structure 302 will now be described. Initially, a process associated with sensor 850 may be performed. The process may comprise, for example, transmitting a broadband pulse, having a plurality of ultrasound waves across a known frequency range and at known amplitudes and optionally known waveforms, from wave generator 814 toward and across the sensor bond region. The transmitted broadband pulse may traverse the sensor bond region and be received by receiver 816. The broadband pulse received by receiver 816 ("the received broadband pulse") may then be used to determine an integrity of a bond between sensor 850 and structure 302.

As will be understood by a person having ordinary skill in the art, an amplitude of one or more of the ultrasound waves of the broadband pulse may vary depending on the integrity of the bond between sensor 850 and structure 302. For example, an amplitude of an ultrasound wave of a received broadband pulse at a specific frequency that traverses a sensor bond region having a fully bonded sensor may be less than an amplitude of an ultrasound wave of a received broadband pulse at the specific frequency that traverses a sensor bond region having a sensor that is at least partially debonded. Accordingly, in comparison to the amplitudes of ultrasound waves at specific frequencies of a transmitted broadband pulse, amplitudes of ultrasound waves at the specific frequencies of a received broadband pulse may be used to determine an integrity of a bond between sensor 850 and structure 302. Amplitude measurements of one or more ultrasound waves of a received broadband pulse at specific frequencies may result in measured data. Likewise, the presence of a compromised, at least partially disbonded sensor bond region may result in a degenerate or corrupted waveform of one or more ultrasound waves of the received broadband pulse. Further, in a similar manner as described above, the measured data may be compared to known reference data in order to determine a condition of a bond between sensor 850 and structure 302. More specifically, an amount of bond (e.g., a percentage of bond) between sensor 850 and structure 302 may be determined. It is noted that material properties (i.e., material types and thicknesses) of each of sensor 850, structure 302, and bonding agent 304 may determine at which specific frequencies an amplitude of an ultrasound wave may vary.

Figure 13:
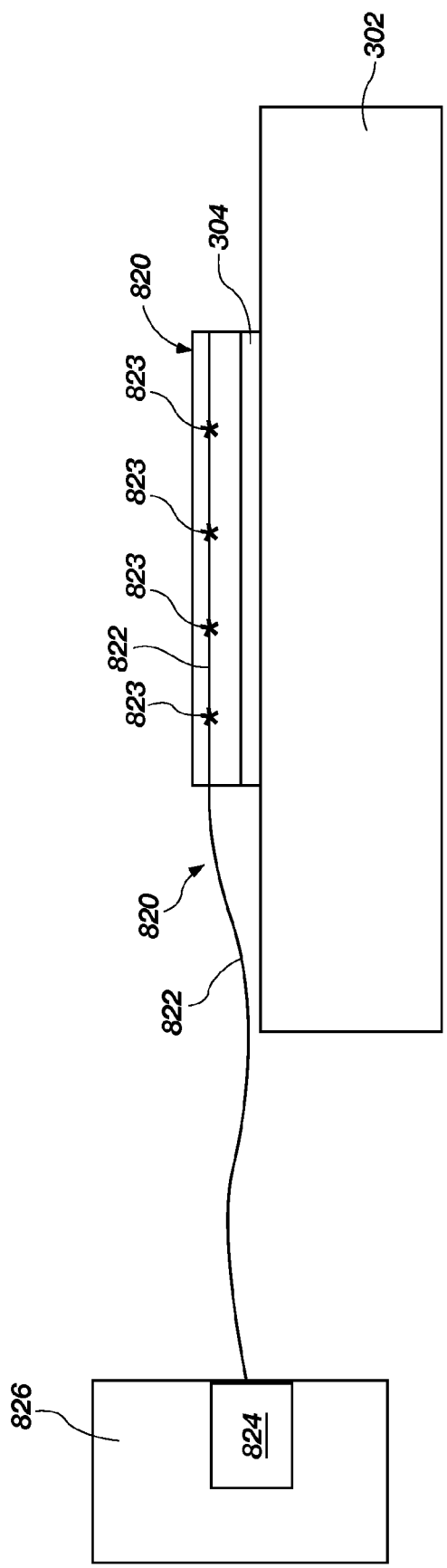
FIG. 13 illustrates a system including an optical sensor bonded to a structure, in accordance with an embodiment of the present invention.

FIG. 13 illustrates a system 819 including an optical sensor 820 bonded to structure 302 via bonding agent 304 and including one or more optical fibers 822. As understood by one having ordinary skill in the art, optical fibers may be configured to measure one or more physical parameters such as, for example, strain, temperature, and pressure. As such, by way of example only, optical sensor 820 may comprise a fiber optic strain gauge, a fiber optic temperature gauge, a fiber optic pressure gauge, or any combination thereof. As is also understood by one having ordinary skill in the art, optical fibers may include periodically spaced changes in the refractive index (e.g., fiber Bragg gratings 823) in the core of an optical fiber. These periodic changes may be configured to reflect a narrow range of specific frequencies of light, while absorbing other frequencies of light. Further, as known in the art, a reflected signal (i.e., reflected light) may be compared with a transmitted signal (i.e., transmitted light) to determine differences between the two signals. The signal differences may be correlated to various physical parameters in order to determine a physical parameter exhibited by a structure to which optical sensor 820 is attached.

A contemplated method of utilizing system 819 to determine integrity of a bond between optical sensor 820 and structure 302 will now be described. Initially, a process associated with sensor 820 may be performed. By way of example only, the process may comprise applying one or more stimuli to optical sensor 820. Furthermore, during application of the one or more stimuli, after termination of the one or more stimuli, or a combination thereof, one or more physical properties associated with optical sensor 820 may be monitored. Stated another way, an effect of the one or more stimuli on optical sensor 820 may be monitored.

More specifically, for example, the contemplated method may include applying a thermal shock to optical sensor 820 in a manner so as to heat optical sensor 820 without heating structure 302 to any substantial or detectable extent. For example only, a light source 824 may transmit light into optical fiber 822 at a frequency selected to enable the transmitted light to be absorbed into one or more elements in the core of optical fiber 822 and, more specifically by fiber Bragg gratings 823. As a result, optical sensor 820 may be heated. Furthermore, during application of a thermal shock to optical sensor 820 (i.e., the transmission and absorption of light within optical fibers 822), after termination of the thermal shock, or a combination thereof, an output response of optical sensor 820 may be monitored. More specifically, light source 824 may transmit light into optical fibers 822 within a range of specific frequencies to enable the transmitted light to pass through optical fibers 822 and be reflected back to a sensor interface 826, which may encompass any suitable optoelectronic circuitry and processing equipment necessary to perform operations including receiving and/or analyzing the reflected signals (reflected light) from the optical sensor 820. As another approach to determining bond condition of an optical sensor 820 using thermal shock, if the sensor comprises an outer metallic sheath, a current or voltage may be applied to the sheath to rapidly heat the optical sensor.

As will be understood by a person having ordinary skill in the art, upon application of heat thereto, optical sensor 820 may attempt to expand. However, because a fully bonded optical sensor may be constrained more than an optical sensor that is at least partially disbonded, the fully bonded optical sensor may be prevented from expanding to the same degree as the optical sensor that is at least partially disbonded. As a result, a fully bonded optical sensor may measure a different amount of strain or pressure than an optical sensor that is at least partially disbonded. For example, a fully bonded fiber optic strain sensor may measure a lesser amount of strain than a fiber optic strain sensor that is at least partially disbonded. Furthermore, because structure 302 may function as a heat sink, a temperature measured by a fully bonded optical sensor may be less than a temperature measured by an optical sensor that is at least partially disbonded. Moreover, the temperature of an optical sensor that is at least partially debonded will decay at a slower rate in comparison to a fully bonded optical sensor.

Physical property measurements associated with optical sensor 820 taken during application of a thermal shock, taken after the application of the thermal shock, or any combination thereof, may result in measured data. Thereafter, in a similar manner as described above, the measured data may be compared to reference data in order to determine a condition of a bond (e.g., a percentage of bond) between optical sensor 820 and structure 302.

Figure 14:
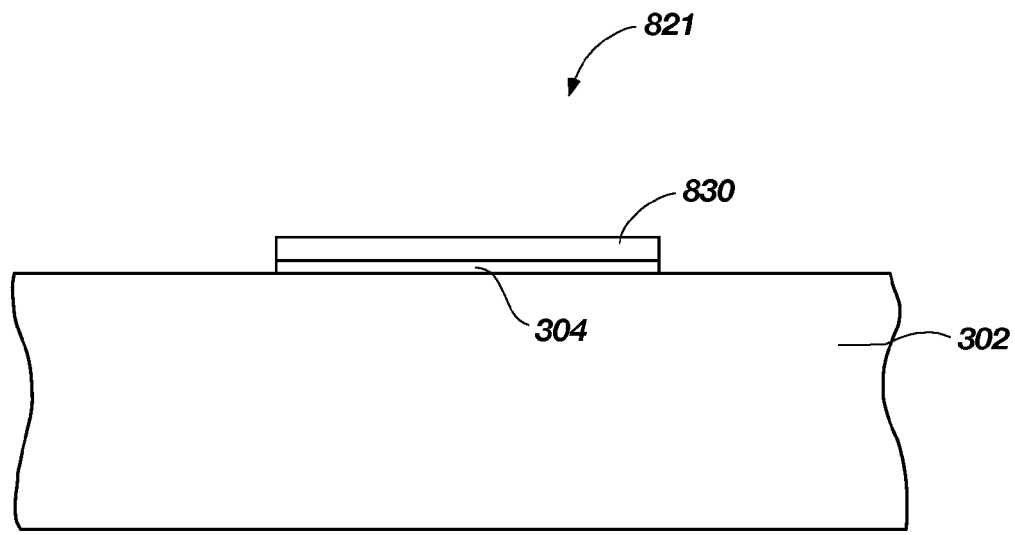
FIG. 14 illustrates a system including a temperature sensor bonded to a structure, according to an embodiment of the present invention.

FIG. 14 illustrates a system 821 including a temperature sensor 830 bonded to structure 302 via bonding agent 304. By way of example only, temperature sensor 830 may comprise a bonded foil temperature sensor, a thermocouple, a resistance temperature detector (RTD), a thermistor, or a fiber optic temperature sensor. To determine integrity of a bond between temperature sensor 830 and structure 302, initially, a process associated with temperature sensor 830 may be performed. The process may include, for example, applying one or more stimuli to temperature sensor 830. Furthermore, during application of the one or more stimuli, after termination of the one or more stimuli, or a combination thereof, one or more physical properties of temperature sensor 830 may be monitored.

More specially, for example, temperature sensor 830 may be initially heated by applying a thermal shock thereto for a short duration by any method disclosed herein, such as photo flash heating, electrical heating, external heating, or heating via optical fibers. Furthermore, during application of a thermal shock to temperature sensor 830, after termination of the thermal shock, or both, a temperature associated with temperature sensor 830 (i.e., a temperature measured by temperature sensor 830 or an actual temperature of temperature sensor 830) may be monitored over time. Stated another way, a shift in the associated temperature and the rate of decay of the associated temperature may be monitored over time. Based on the general principles of heat transfer, it will be understood by one having ordinary skill in the art that if a sensor is at least partially debonded from a structure, the temperature of the sensor will increase a greater amount during application of the thermal shock than it would have had the sensor been fully bonded to the structure. Furthermore, after termination of the thermal shock, a temperature of a sensor that is at least partially debonded will decay at a slower rate in comparison to a fully bonded sensor.

Measurements associated with temperature sensor 830 taken during the application of a thermal shock, taken after termination of the thermal shock, or both, may result in measured data. Thereafter, in a similar manner as described above, the measured data may be compared to reference data in order to determine an amount of bond (e.g., a percentage of bond) between temperature sensor 830 and structure 302.

Figure 15:
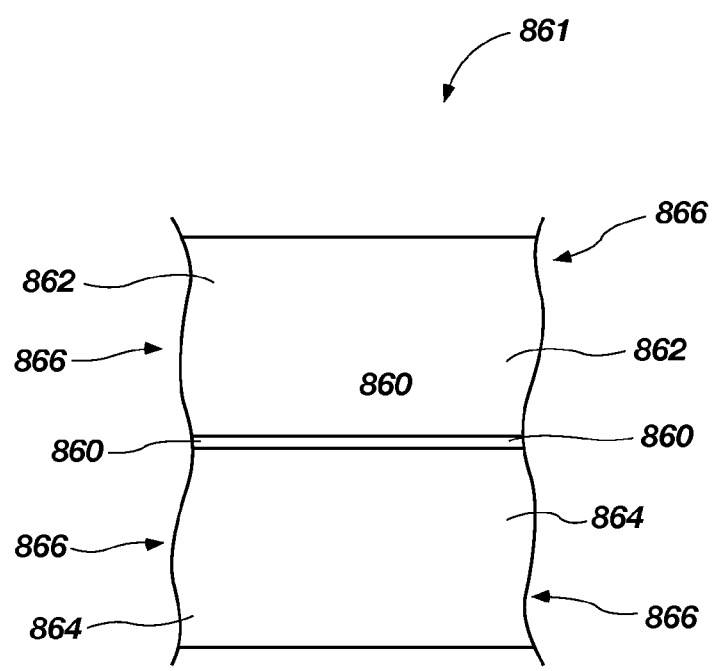
FIG. 15 illustrates a system including a sensor embedded between two adjacent layers of a composite structure, in accordance with an embodiment of the present invention.

FIG. 15 illustrates a system 861 including a sensor 860 embedded between two adjacent layers 862 and 864 of a composite structure 866. Composite structure 866 may comprise, by way of non-limiting example, any structure comprising a plurality of bonded laminate. More specifically, composite structure 866 may comprise a plurality of carbon, glass or other fibers, which may optionally be formed into tows or fabric, mutually bonded together as by a resin system. As non-limiting examples, sensor 860 may be configured to measure strain, pressure, temperature, or any combination thereof. A contemplated method of utilizing sensor 860 to detect a delamination between adjacent layers 862 and 864 of composite structure 866 will now be described. Initially, a process associated with sensor 860 may be performed, such as applying one or more stimuli to sensor 860. As a more specific example, a process may comprise applying a thermal shock to sensor 860 by any suitable method disclosed herein. Furthermore, during application of the one or more stimuli, after termination of the one or more stimuli, or both, an affect of the one or more stimuli on sensor 860 may be monitored. More specifically, a temperature measurement associated with sensor 860 may be monitored.

As will be understood by a person having ordinary skill in the art, the thermal conductivity between a sensor and adjacent layers of a composite structure that are not delaminated will be greater than the thermal conductivity between a sensor and adjacent layers, which are at least partially delaminated. Stated another way, because air, vapor, or vacuum may exist between a sensor and a composite structure having a delaminated layer proximate the sensor, the thermal conductivity between the sensor and the composite structure will be less than in comparison to a composite structure that does not include a delamination. Accordingly, during an application of a thermal shock, a temperature registered by a sensor proximate a delamination may be greater than it be would have been if the delamination did not exist. Moreover, after termination of the thermal shock, the temperature registered by the sensor proximate the delamination will decay at a slower rate in comparison to a case wherein no delamination exists. Measurements associated with sensor 860 taken during application of a thermal shock, taken after termination of the thermal shock, or both, may result in measured data, which may be used to determine a condition of adjacent layers 862 and 864. More specifically, the measured data may be compared to reference data to determine whether a layer proximate sensor 860 (i.e., layer 862 or layer 864) has delaminated.

Figure 16:
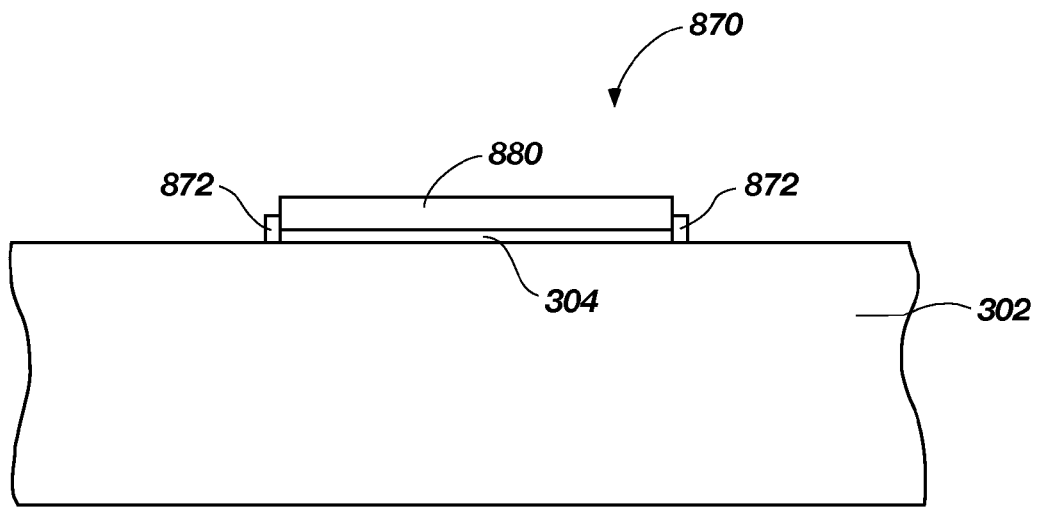
FIG. 16 illustrates a system including a sensor bonded to a structure and a capacitance meter operably coupled to each of the sensor and the structure, in accordance with an embodiment of the present invention.

In accordance with another embodiment of the present invention, integrity of a bond between a sensor and a structure may be determined by measuring an amount of capacitance between the sensor and the structure. FIG. 16 illustrates another system 870 according to an embodiment of the present invention. System 870 includes a sensor 880, which is bonded to structure 302 via bonding agent 304. System 870 further includes one or more capacitance meters 872 configured to measure a capacitance between sensor 880 and structure 302. According to one embodiment, capacitance meter 872 may be directly coupled to each of sensor 880 and structure 302. According to another embodiment, capacitance meter 872 may be positioned remote from and electrically coupled to each of sensor 880 and structure 302.

It is noted that in order to measure a capacitance between sensor 880 and structure 302, structure 302 should comprise a conductive material, such as, for example, a metal or carbon based composite and bonding agent 304 should comprise a dielectric material so that, in combination, sensor 880, bonding agent 304 and structure 302 respectively form one electrode, the dielectric and another electrode of a capacitive structure. As an example, according to one embodiment wherein sensor 880 comprises a strain gauge, a constantan foil of the strain gauge may form one electrode, structure 302 may form another electrode, and a polyimide layer of the strain gauge and bonding agent 304 may form a dielectric.

As will be understood by a person having ordinary skill in the art, an amount of capacitance between a structure and a sensor fully bonded to the structure will be greater than an amount of capacitance between a structure and a sensor that is at least partially disbonded from the structure. Stated another way, as a sensor debonds from a structure, a distance between the sensor and the structure may increase, causing a capacitance between the sensor and structure to decrease. Capacitance measurements obtained from the capacitance sensor 872 may result in measured data, which may be compared to known reference data in order to determine if sensor 880 has at least partially debonded from structure 302.

Figure 17:
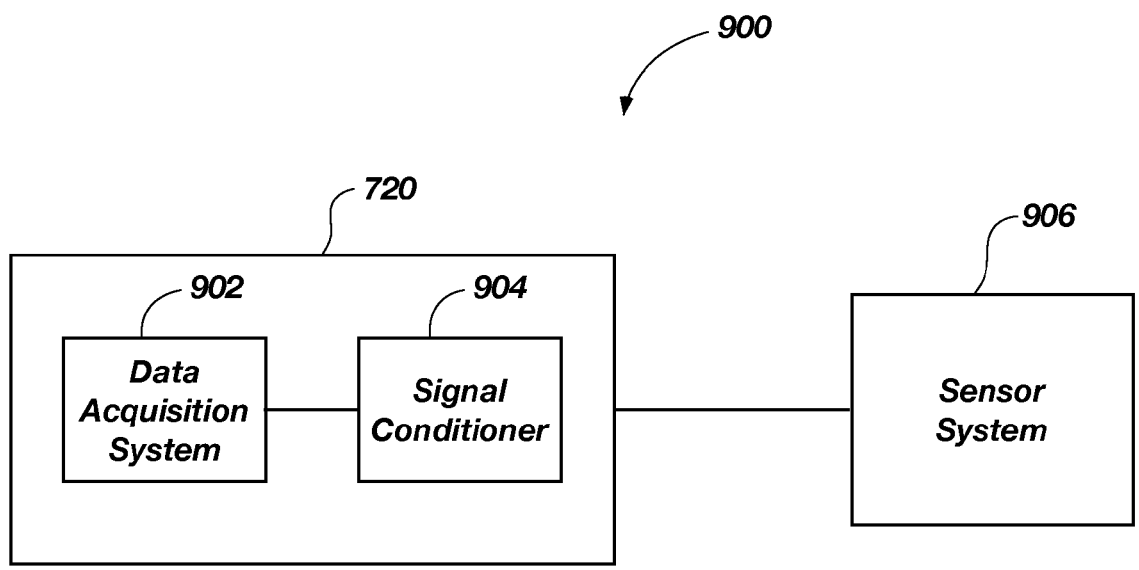
FIG. 17 illustrates a system including the sensing system of FIG. 9 coupled to a sensor system, in accordance with an embodiment of the present invention.

FIG. 17 illustrates another system 900 including sensing system 720, as described above with reference to FIG. 9, coupled to a sensor system 906. Sensing system 720 may comprise a data acquisition system 902 and a signal conditioner 904. According to various embodiments, sensor system 906 may comprise sensor 710 as described above with reference to FIG. 9. Furthermore, according to other embodiments, sensor system 906 may comprise system 800, system 810, system 812, system 819, system 821, system 861, or system 870, each of which has been described above.

Figure 18:
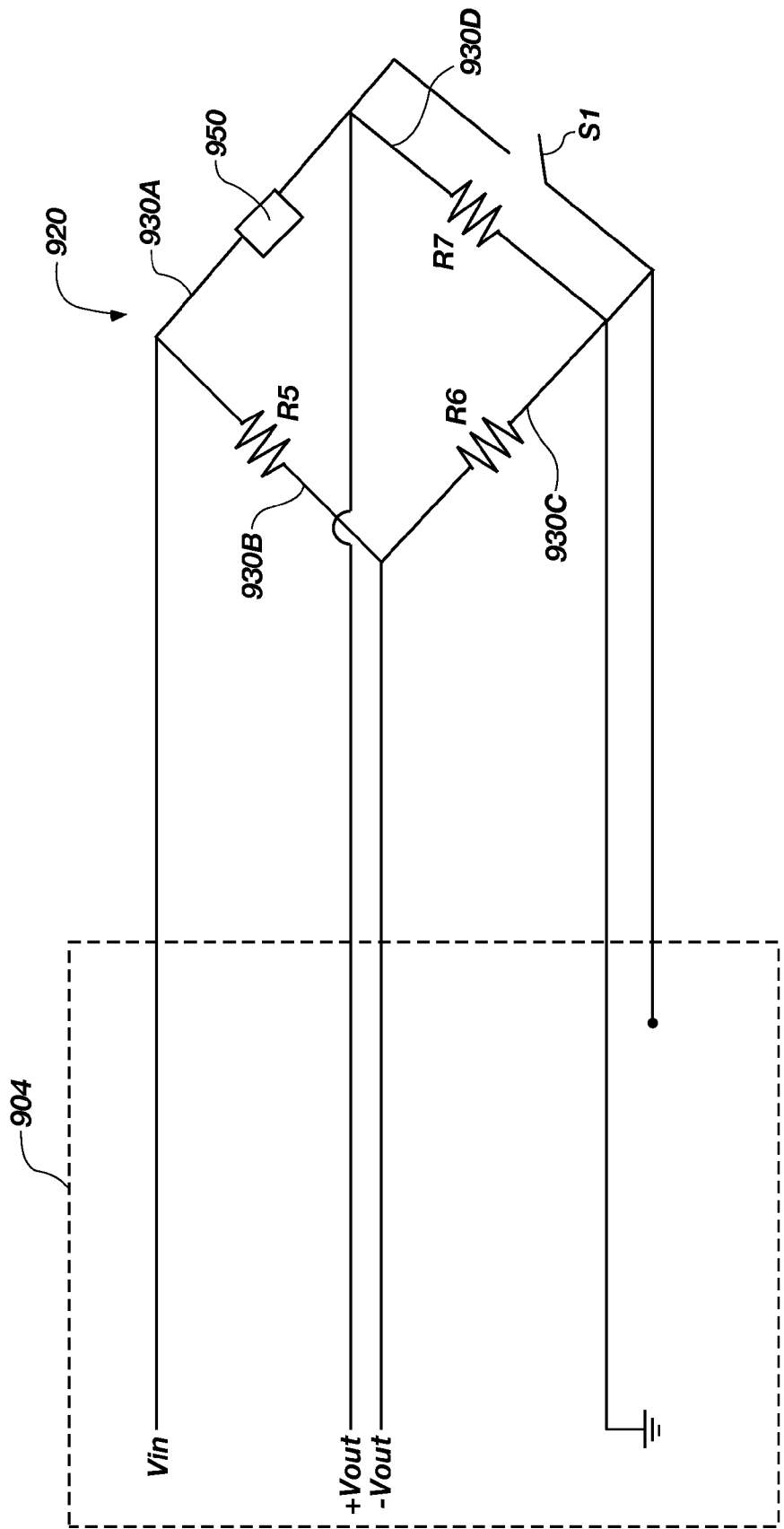
FIG. 18 illustrates a signal conditioner coupled to a sensor within a measurement circuit including a switch, in accordance with an embodiment of the present invention.
Figure 19:
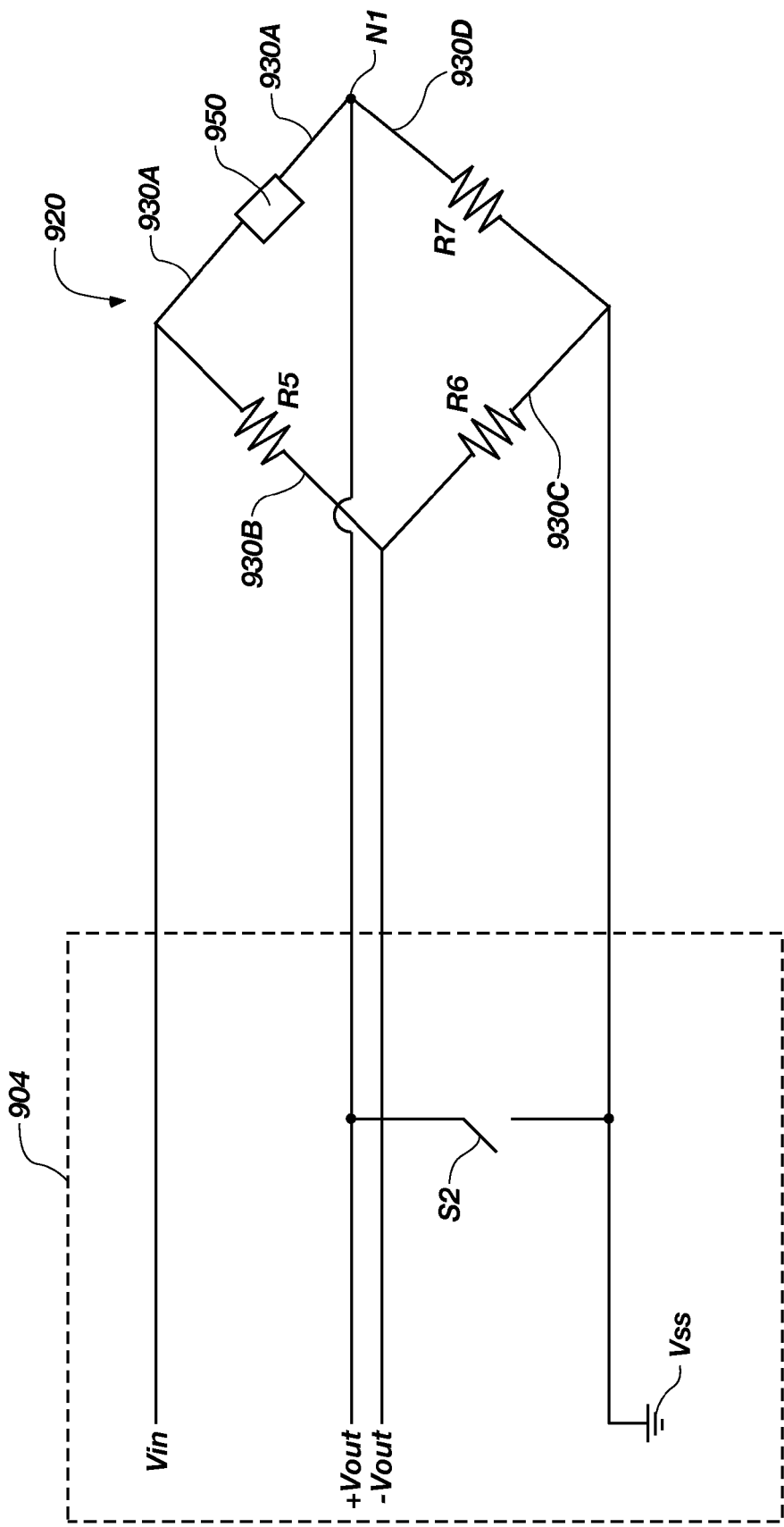
FIG. 19 illustrates a signal conditioner including a switch and coupled to a sensor within a measurement circuit, in accordance with an embodiment of the present invention.

Signal conditioner 904 may be operably coupled to a sensor (e.g., sensor 710, sensor 850, sensor 820, sensor 830, sensor 860, or sensor 880) within system 906 and may be configured to transmit a signal to a sensor to initiate application of a stimulus thereto (e.g., applying a thermal shock to a strain gauge). According to one embodiment, signal condition 904 may include circuitry configured to apply a thermal shock to the sensor. For example, with reference to FIGS. 17 and 18, signal conditioner 904 may include a Wheatstone bridge measurement circuit 920 having four branches 930A, 930B, 930C, and 930D. Branch 930A includes a sensor 950 (e.g. a strain gauge), and branches 930B, 930C, and 930D may include resistors R5, R6, and R7, respectively. In one contemplated operation, after sensor 950 has reached a steady-state thermal condition, a switch S1, which is in parallel with resistor R7, may be closed to short out resistor R7. As a result, an entire input voltage Vin may be applied across sensor 950 and, thus, the power dissipation in sensor 950 may be increased. Switch S1 may remain closed for a sufficient amount of time to heat sensor 950 without heating a structure to which sensor 950 is attached. Thereafter, switch S1 may be opened and sensor 950 may return to a steady-state thermal condition. According to another embodiment as illustrated in FIG. 19, a switch S2, which is positioned within signal conditioner 904, may be closed to couple a node N1 to a ground voltage Vss. As a result, an entire input voltage Vin may be applied across sensor 950 and, thus, the power dissipation in sensor 950 may be increased. Switch S2 may remain closed for a sufficient amount of time to heat sensor 950 without heating a structure to which sensor 950 is attached. Thereafter, switch S2 may be opened and sensor 950 may return to a steady-state thermal condition.

Signal conditioner 904 may also be configured to receive an output signal from a sensor (i.e., sensor 710, sensor 850, sensor 820, sensor 830, sensor 860, or sensor 880) or a detection device (infrared sensor 802, receiver 816, sensor interface 826, capacitance sensor 872), condition the output signal (e.g., amplify, filter, etc.) and convey the conditioned signal to data acquisition system 902. Moreover, sensing system 720 may be configured to transmit a control signal to a device (e.g., illumination source 804, wave generator 814, light source 824, or capacitance sensor 872) to initiate a process associated with a sensor. Additionally, sensing system 720 may be configured to transmit one or more control signals to infrared sensor 802, receiver 816, or sensor interface 826 to control operation thereof, for example, to sense desired parameters at selected intervals.

The systems and methods of the various embodiments described herein have a multitude of different applications. As non-limiting examples, the various embodiments of the present disclosure may be utilized within industrial process health monitoring applications, vehicular or static structural health monitoring applications, and rocket motor health monitoring applications. For example, at any time before initiation of an event (e.g., a product run of an industrial process, an aerospace vehicle flight, or a rocket motor ignition) has begun, during an event, or both, a bond integrity of one or more sensors within a system (e.g., a industrial process health monitoring system, aerospace vehicle health monitoring system, or rocket motor test system) may be tested. One non-limiting example application of embodiments of the present disclosure to an industrial process is prior to a refinery restart after scheduled or unscheduled maintenance or repair. One non-limiting example application of embodiments of the present disclosure to aerospace vehicles is between and during flights, to both conventional metal and to composite aerospace structural components such as fuselages, fuel tanks, engine housings, airfoil structures and connections between such structural components. One non-limiting example application of embodiments of the disclosure to rocket motor health monitoring applications is preflight qualification of pressure vessels such as liquid fuel tanks for liquid fuel rocket motors and rocket motor casings of solid fuel rocket motors.

More specifically, a computer (e.g., sensing system 720 illustrated in FIGS. 9 and 17) may initiate application of a stimulus (e.g., heat) to the one or more sensors. Furthermore, during application of the stimulus, after termination of the stimulus, or both, a response associated with the one or more sensors may be monitored and analyzed by the computer according to one or more of the various methods described herein to determine bond integrity of the one or more sensors. It is contemplated that in use, a sensor system for a structure or series of cooperatively coupled structures of interest may include dozens, hundreds or even thousands of sensors, the bond integrity of each of which may be monitored on a periodic basis prior to initiation of selected events, or in response to external stimuli sensed by other sensors associated with the sensor system. For example, an ambient temperature, ambient pressure, or ambient radiation sensor may be used to trigger a sensor bond verification sequence prior to acquiring data from the bonded sensors themselves of the condition or conditions they are configured to sense.

Embodiments of the disclosure employed in static structure health monitoring applications may be controlled by a sensing system 720 so that sensor bond integrity is measured at selected time intervals or, for example, in response to an external stimulus such as a seismic shock detected by one or more accelerometers associated with sensing system 720. By way of non-limiting example, the structural integrity of relatively high-stress static structures, including but not limited to suspension bridges, overpasses, elevated entrance and exit ramps, high-rise buildings, submerged and subterranean tunnels, stadiums, pipelines, electrical grid components (e.g., high tension power lines and supporting structures, transformers and switching components), nuclear power plants, and dams may be monitored by various sensors secured to, or embedded within, one or more structural components. Such structures may be subject to various adverse environmental conditions over an intended or predicted life of a structure, including impact, vibration, pressure and temperature extremes and fluctuation, corrosive elements (e.g. salt and other corrosive substances), and radiation, any of which or a combination of which may substantially and catastrophically shorten the intended or predicted life. Thus, accurate assessment of structural integrity and degradation thereof is highly desirable, to avoid loss of life or injury, as well as direct and consequential property damage. Such accurate assessment may be compromised by partial or complete sensor debonding. Use of embodiments of the disclosure may be employed to identify compromised sensors and prompt repair or replacement thereof, where possible.

Yet another application of embodiments of the present disclosure is in qualification of static components of military vehicles, such as integrity of composite armor comprising a plurality of layers for use in armored vehicles and to be worn by military and law enforcement personnel. In such an application, a plurality of sensors may be placed in an armor panel or in various panels of (for example) an armored vest, the plurality of sensors being connected to a wiring harness which, in turn, may be connected to a sensor system for determining armor integrity before or after a combat mission, such determination being preceded by a sensor bond integrity determination sequence.

In addition, embodiments of the invention may be employed to initiate deployment of a redundant, backup sensor placed in a sensor-equipped structure at approximately the same location as a sensor identified as bond-compromised. In other words, if a given sensor's bond is identified as compromised to a point where sensor output is no longer accurately indicative of a structure's to-be-sensed state, another identical sensor at substantially the same location and determined to have adequate bond integrity may be employed to take sensor readings in lieu of the bond-compromised sensor. Such a technique may be particularly desirable to use in applications where sensors are remotely placed and inaccessible for repair and replacement.

As noted above, various embodiments of the present invention may comprise comparing measured data to model data, which may generated by performing tests on a model sensor. The following description illustrates methods of generating an electro-thermal model of a particular strain gauge in a quasi steady-state and a transient state. To generate an electro-thermal model of a particular strain gauge in quasi steady-state, the change in resistance of a constantan filament of the particular strain gauge in an unconstrained state (i.e., debonded state) as a function of temperature may be determined. In a constrained state (i.e., bonded state) the fractional change in resistance of the constantan filament of the particular strain gauge may be defined as:

$$\Delta R/R = Cf^*\Delta T + Gf^*\Delta \epsilon; \quad (1)$$

wherein Cf is the change in resistance of the constantan filament as a function of temperature, Gf is the gage factor of the particular strain gauge, $\Delta T$ is the change in temperature, and $\Delta \epsilon$ is the strain of the constantan filament of the particular strain gauge.

Further, if there is no intentional strain applied to a substrate to which the particular strain gauge is attached, the change in resistance of the constantan filament may be defined as:

$$\Delta R/R = Gf^*\Delta \epsilon_a; \quad (2)$$

wherein $\Delta \epsilon_a$ is the apparent strain of the particular strain gage, which may be provided by the manufacturer of the particular strain gage.

Setting equation (1) equal to equation (2) gives the following equation:

$$Cf = -Gf^*(\Delta \epsilon - \Delta \epsilon_a))/\Delta T; \quad (3)$$

Additionally, the strain of the constantan filament of the particular strain gauge may be defined as:

$$\Delta \epsilon = (\alpha s - \alpha f)^*\Delta T; \quad (4)$$

wherein $\alpha s$ is the thermal expansion coefficient of a substrate to which the particular strain gauge is attached and of is the thermal expansion coefficient of the constantan filament.

Equations (3) and (4) may be combined into the following equation (5) to solve for Cf (i.e., the change in resistance of the constantan filament as a function of temperature):

$$Cf = Gf^*(d\epsilon_a/dT - \alpha s + \alpha f); \quad (5)$$

As noted above, $\epsilon_a$ represents the apparent strain of the constantan filament and may be represented in a polynomial form as follows:

$$\epsilon_a = A + B^*T + C^*T^2 + D^*T^3 + E^*T^4; \quad (6)$$

wherein the variables A, B, C, and D may be provided by the manufacturer of the particular strain gage.

Accordingly, the change in resistance of the constantan filament in an unbounded state as a function of temperature may be represented by the following equation:

$$Cf = Gf^*(B + 2^*C^*T + 3^*D^*T^2 + 4^*E^*T^3 - \alpha s + \alpha f); \quad (7)$$

Furthermore, to generate an electro-thermal model of a particular strain gauge in a transient state, equation (5) may be used to solve for apparent strain as follows:

$$d\epsilon_a/dT = Cf/Gf + \alpha - \alpha f; \quad (8)$$

wherein $\alpha$ represents the thermal expansion coefficient, which may vary depending on if the strain gauge is bonded (i.e., $\alpha = \alpha s$), disbonded (i.e., $\alpha = \alpha f$), or constrained with no temperature change in the substrate (i.e., $\alpha = 0$).

Taking the integral of equation (8) over a temperature range of interest may give the following equation for an apparent strain of an electro-thermal model of a particular strain gauge in a transient state:

$$\in a = \int_{T_i}^{T} (Cf/Gf + \alpha - \alpha f) dT; \quad (9)$$

Specific embodiments have been shown by way of example in the drawings and have been described in detail herein; however, the invention may be susceptible to various modifications and alternative forms. It should be understood that the invention is not intended to be limited to the particular forms disclosed. Rather, the invention includes all modifications, equivalents, and alternatives falling within the scope of the invention as defined by the following appended claims, and their legal equivalents.

What is claimed is:

1. A method of verifying sensor bond integrity, comprising:
   applying one or more stimuli to a sensor bonded to a structure;
   monitoring a physical property associated with the sensor responsive to the one or more stimuli; and
   determining an amount of bond between the sensor and the structure based on the monitored physical property, wherein applying one or more stimuli comprises applying a thermal shock to the sensor, and wherein applying a thermal shock comprises at least one of applying an increased or pulsed voltage and an increased or pulsed current to the sensor.

2. The method of claim 1, wherein monitoring a physical property associated with the sensor comprises monitoring a temperature of the sensor with an infrared sensor.

3. The method of claim 1, wherein monitoring a physical property associated with the sensor comprises monitoring one of a strain measured by the sensor and a temperature measured by the sensor.

4. The method of claim 1, wherein monitoring a physical property associated with the sensor comprises monitoring a rate of change of a temperature in the sensor.

5. A computer-readable media storage medium storing instructions that, when executed by a processor, cause the processor to perform instructions for operating a sensing system, the instructions comprising the method of claim 1.

6. A structure, comprising:
   at least one sensor bonded to one or more components of the structure to measure a physical property thereof;
   a sensing system operably coupled to the at least one sensor and configured to perform the method of claim 1.

7. The structure of claim 6, wherein the at least one sensor comprises at least one redundant sensor at substantially the same location on or within the structure as the at least one sensor, and the sensing system is configured to employ the at least one redundant sensor to measure the physical property using the at least one redundant sensor if the amount of bond between the at least one sensor and the bone or more components is determined to be insufficient to provide sensed output of the physical property of sufficient accuracy.

8. A method of measuring bond integrity between a sensor and a structure, comprising:
   performing a process associated with a sensor bonded to a structure;
   generating measured data in response to the process; and
   comparing the measured data to known reference data to determine an integrity of a bond between the sensor and the structure, wherein performing a process associated with a sensor comprises transmitting a broadband pulse having a plurality of ultrasound waves across a frequency range and at least one of known amplitudes and known waveforms toward a surface of the structure having the bonded sensor adjacent thereto.

9. The method of claim 8, wherein generating measured data comprises receiving the broadband pulse with a receiver after the broadband pulse has traversed adjoining surfaces of the sensor and the structure.

10. The method of claim 8, wherein comparing comprises comparing at least one of the known amplitudes of the ultrasound waves and the known waveform of the ultrasound waves of the transmitted broadband pulse to associated at least one of measured amplitudes of the ultrasound waves and measured waveforms of the ultrasound waves of the received broadband pulse.

11. A system, comprising:
   at least one sensor bonded to a structure; and
   a sensing system operably coupled to the at least one sensor and configured to perform the method of claim 8.

12. The system of claim 11, wherein the sensing system is configured to transmit a control signal to a wave generator to initiate the process to be performed on the sensor bonded to the structure.

13. A method of determining a condition of a bond between a sensor and a structure, comprising:
   monitoring an effect of one or more stimuli applied to a sensor bonded to a structure; and
   determining a condition of a bond between the sensor and the structure based on the effect of the one or more stimuli, wherein the structure is a composite structure, and monitoring an effect of one or more stimuli comprises monitoring the effect of the one or more stimuli applied to the sensor embedded between adjacent layers of the composite structure, and wherein determining a condition comprises determining whether at least two of the adjacent layers of the composite structure have mutually delaminated.

14. A system, comprising:
   a sensor system including at least one sensor bonded to a structure; and
   a sensing system coupled to the sensor system and including a signal conditioner, the sensing system configured to perform the method of claim 13.

15. The system of claim 14, wherein the one or more stimuli comprises a thermal shock and wherein the sensing system is further configured to transmit a control signal to a light source to apply the thermal shock to the at least one sensor.

16. The system of claim 14, wherein the one or more stimuli comprises a thermal shock and wherein the signal conditioner comprises circuitry configured to apply the thermal shock to the at least one sensor.

17. The system of claim 16, wherein the circuitry comprises a Wheatstone bridge circuit including a switch configured to short out a resistor in series with the at least one sensor to enable for the thermal shock to be applied to the at least one sensor.

* * * * *

UNITED STATES PATENT AND TRADEMARK OFFICE
CERTIFICATE OF CORRECTION

PATENT NO. : 8,708,555 B2
APPLICATION NO. : 12/631600
DATED : April 29, 2014
INVENTOR(S) : John L. Shipley et al.

It is certified that error appears in the above-identified patent and that said Letters Patent is hereby corrected as shown below:

In the specification:
    COLUMN 1, LINE 5, change "RELATED APPLICATIONS" to --RELATED APPLICATION--
    COLUMN 18, LINE 3, change "may generated" to --may be generated--

In the claims:
CLAIM 7, COLUMN 19, LINE 54, change "the bone" to --the one--
CLAIM 10, COLUMN 20, LINE 14, change "waveform" to --waveforms--

Signed and Sealed this
Twenty-fourth Day of November, 2015

Michelle K. Lee
*Director of the United States Patent and Trademark Office*